April 28, 1942. H. L. McCLUNG Plant Pat. 511
ROSE
Filed Aug. 4, 1939
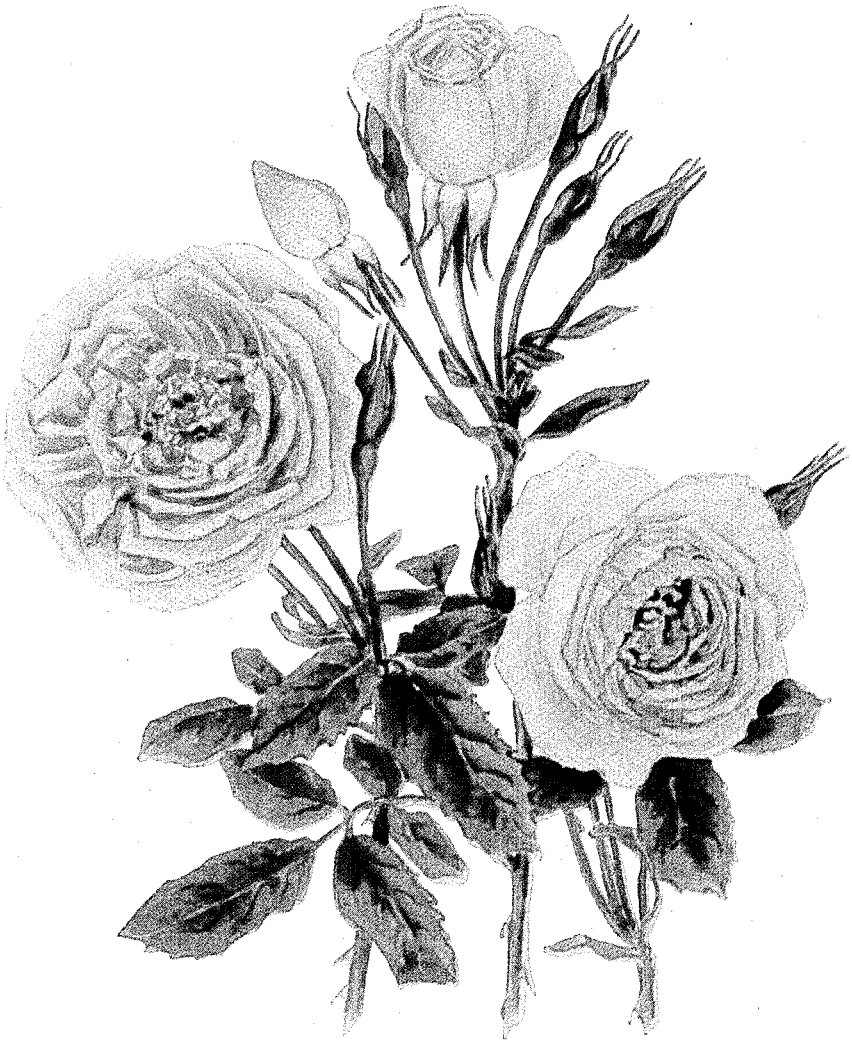
Inventor
Henary L. McClung,
By J. Stanley Burch Attorney Patented Apr. 28, 1942

Plant Pat. 511

UNITED STATES PATENT OFFICE

511

ROSE

Henary L. McClung, Tyler, Tex.

Application August 4, 1939, Serial No. 288,422

1 Claim. (Cl. 47—61)

The present invention relates to a new variety of rose which first appeared as a sport of the well known Betty Uprichard rose bush.

Buds from this sport were inserted in the rootstock of the *Multiflora japonica* shortly after discovery, and the process of budding has been followed continuously during each budding season with the result that the blooms have run true to type.

The present new variety of rose occurs both as a bush and as a semi-climber. In other words, some of the plants produced from these buds will grow to a height of two or three feet, while other plants from these buds will grow to a height of some six or seven feet, the small bushes being termed bush roses and the larger ones being termed semi-climbers. The blooms on both types of plants are the same size and color, and the plant is always a prolific and thrifty grower and bloomer.

The bloom of the present new variety of rose is a large double-petal bloom of a bright red color and grows on long straight stems or canes. When fully open, the bloom is about 3½ inches in diameter and is unusually fragrant, although it does not remain fresh as long after cutting as the usual rose and fades to a rose purple. The buds are oblong and very hard or solid. The present rose is shown in full color in the accompanying drawing.

Peculiar and distinguishing characteristics of the present rose plant variety may be listed as follows:

*Flower*

Blooming habit: It is ever-blooming profusely.

Bud: Of medium size—very hard, or solid—medium length pointed; unaffected by hot or wet weather. Bright red or scarlet in color.

The bloom: When fully expanded, it measures 3½" in diameter.

Borne: Singly and in clusters.

Stems: Long straight and of medium strength.

Form: When first open—low center; outer petals curl back, inner petals are smaller and curl inward.

Petalage: Double—full but open center. Number of petals under normal conditions, 26.

Color: Center of flower (stamen) lemon color. All petals are of bright red, or scarlet color, both sides of petals bearing same shade of red—no variation in color of outer and inner petals.

Variegations: None.

Discolorations: About third day after full expansion, bloom fades to rose purple.

Petals: Thin texture. Slightly affected by heat, and by wet weather.

Appearance of Petals: Shiny, both inside and out.

Form of Petals: Oval.

Arrangement: Informal and with inner petals curled inwardly, while outer petals curl outwardly.

Fragrance: Unusually strong and sweet, and lasting throughout all stages of the bloom.

Lasting quality: On the plant, long; as cut flower, shorter than most varieties.

*The plant*

Form: Bush and semi-climber.

Growth: A hardy and thrifty grower—a great number of branches, but usually uniform and rounding;—occurring as a bush rose, and growing to a height of from 2½ to 3 feet, and also as a semi-climber, and growing to a height of from 6 to 7 feet. The extreme variability in the height of individual plants is believed to be inherent in the clon.

Foliage: Five leaflets. Large size and dark green in color—leaflets glossy on upper side, ribs and veins slightly visible, and underside—rough, and with ribs and veins prominent.

Edge: Edge of leaflets, serrated—sawlike teeth varying in size and uneven.

Thorns: Quantity: on main stalk, unusually large. On branches and laterals from stalk, still more than on other varieties—all thorns have long narrow base and are hooked downward.

What I claim as new is:

The rose plant variety herein shown and described, and which is characterized by the fact that it is profusely ever-blooming and occurs both as a bush and as a semi-climber having a medium amount of dark green foliage and an unusually large number of small thorns, and whose blooms are borne singly and in clusters and occur on long straight stems and are of a large double-petal variety of a bright red color, each bloom having a full open center and about 26 shiny petals which curl back, the inner petals being relatively small and curling inwardly and the larger outer petals curling outwardly.

HENARY L. McCLUNG.